US006429329B1

(12) United States Patent
Aaronson et al.

(10) Patent No.: US 6,429,329 B1
(45) Date of Patent: Aug. 6, 2002

(54) SYNTHESIS OF A HYDROCARBYLVINYLPHOSPHONIC ACID HYDROCARBYL ESTER

(75) Inventors: Alan M. Aaronson, Fresh Meadows; John Tomko, Dobbs Ferry; Jeffrey E. Telschow, Tarrrytown; Johannes Hermanus Boelee, Irvington; Fred Jaffe, Ossining, all of NY (US)

(73) Assignee: Akzo Nobel NV, Arnhem (NL)

( * ) Notice: Subject to any disclaimer, the term of this patent is extended or adjusted under 35 U.S.C. 154(b) by 1359 days.

(21) Appl. No.: 08/711,135

(22) Filed: Sep. 9, 1996

Related U.S. Application Data

(63) Continuation of application No. 08/386,392, filed on Feb. 10, 1995, now abandoned.

(51) Int. Cl.$^7$ ................................................. C07F 9/40
(52) U.S. Cl. ................................................... 558/142
(58) Field of Search ........................................ 558/142

(56) References Cited

U.S. PATENT DOCUMENTS

| | | | | |
|---|---|---|---|---|
| 2,254,124 A | | 8/1941 | Stevens et al. | 260/500 |
| 2,365,466 A | | 12/1944 | Hamilton | 260/543 |
| 2,579,810 A | * | 12/1951 | Fields | 260/461.1 |
| 3,493,639 A | | 2/1970 | Tavs | 260/969 |
| 4,388,252 A | * | 6/1983 | Dursch et al. | 558/142 |
| 4,427,602 A | | 1/1984 | Kleiner | 260/543 P |
| 4,486,357 A | | 12/1984 | Krause et al. | 260/502.4 R |
| 4,507,249 A | | 3/1985 | Pieper et al. | 260/502.4 R |
| 4,529,559 A | | 7/1985 | Pieper | 260/502.4 R |

FOREIGN PATENT DOCUMENTS

GB 974988 11/1964

OTHER PUBLICATIONS

Morrison and Boyd, Organic Chemistry, 2$^{nd}$ Ed., Allyn and Bacon, Inc., Boston (1966), p. 669.*
M. Yamashita et al. "New Synthesis and Hydroboration of Vinylphosphonates", Bull. Chem. Soc. Jpn., 53, 1625–1628 Jun. (1980).
G. Maas et al., "Substituentenabhängigkeit des Norcaradien/Cycloheptatrien–Gleichgewichtes–untersucht an 7–phosphoryl–und 7–carbonylsubstituierten Systemen", Chem. Ber., 109, 2039–2063 (Month not available) (1976).
P. Tavs et al., "Herstellung und KMR–Spektren Einiger α,β–Ungesättigter Phosphonsäureester", Tetrahedron, vol. 26, pp. 5229 to 5534 (Month not available) (1970).
C. Li et al., "Studies on Organophosphorus Compounds: 68. A New and Facile Synthetic Approach to Alkylidenebisphonates", Tetrahedron Letters, vol. 34, No. 9, pp. 1515–1516 (month not available ) (1993).
J.B. Conant et al., "Addition Reactions of the Phosphorus Halides: V. The Formation of an Unsaturated Phosphonic Acid", J. Amer. Chem. Soc., 44, 2530–2536 (Month not available) (1922).

T. Hirao et al., "Palladium–Catalyzed New Carbon–Phosphorus Bond Formation", Bull. Chem. Soc. Jpn., 55, 909–913 Mar. (1982).
W.E. Krueger et al., "Additions of Trialkyl Phosphites to Nitroalkenes", J. Org. Chem., vol. 43, No. 14, pp. 2877–2879 (Month not available) (1978).
F. Texier–Boullet et al., "An Unexpected Reactivity of Simple Heterogeneous Mixture of γ–Alumina and Potassium Fluoride: 1–Hydroxyalkane Phosphonic Esters Synthesis From Non–Activated Ketones in 'Dry Media'", Tetrahedron Letters, vol. 27, No. 30, pp. 3515–3516 (Month not available) (1986).
R. Engel, ed., Handbook of Organophosphorus Chemistry (Marcel Dekker, New York, (Month not available) (1992), pp. 301 and 355.
V.S. Abramov, "The Reaction of Dialkylphosphorus Acids With Aldehydes and Ketones: A New Method of Synthesizing Esters of Alpha Hydroxyalkylphosphinic Acids", Zh. Obshch. Khim., 22, pp. 709–713 (Month not available) (1952).
F. Texier–Boullet et al., "A Convenient Synthesis of Dialkyl 1–Hydroxyalkanephosphonates Using Potassium or Caesium Fluoride Without Solvent", Synthesis (Communications), Feb. 1982, pp. 165–166.
Chemical Abstracts, vol. 45, Abstract 2855h (Month not available) (1951).
Chemical Abstracts, vol. 46, Abstract 6140h (Month not available) (1952).
Chemical Abstracts, vol. 60, Abstract 10718f (Month not available) (1964).
Chemical Abstracts, vol. 61, Abstract 9524d (Month not available) (1964).
Chemical Abstracts, vol. 73, Abstract 77387w (Month not available) (1970).
Chemical Abstracts, vol. 73, Abstract 88024b (Month not available) (1970).
Chemical Abstracts, vol. 74, Abstract 64277f (Month not available) (1971).

* cited by examiner

Primary Examiner—Laura L. Stockton
(74) Attorney, Agent, or Firm—Richard P. Fennelly

(57) ABSTRACT

A process for the synthesis of a hydrocarbylvinyl-1-phosphonic acid hydrocarbyl ester, such as a 1-phenylvinylphosphonic acid dialkyl ester, which utilizes: (a) the base catalyzed addition (preferably using a nonnucleophilic strong organic base) of a hydrocarbyl phosphite, such as a dialkyl phosphite containing no more than about eight carbon atoms in either of its alkyl groups, to an aldehyde or methyl ketone, such as a phenyl ketone, as exemplified by acetophenone, to form a hydrocarbyl 1-hydroxy-1-hydrocarbylphosphonate, such as a dialkyl 1-hydroxy-1-phenylalkylphosphonate compound; (b) the acid-catalyzed esterification (preferably acetylation) of the compound from (a) with an acid anhydride to form an acylated intermediate; and (c) the removal of carboxylic acid (preferably at a temperature of from about 50° C. to about 215° C. under reduced or atmospheric pressure) from the intermediate from (b) to form the desired hydrocarbylvinylphosphonic acid hydrocarbyl ester, such as a 1-phenylvinylphosphonic acid dialkyl ester.

25 Claims, No Drawings

SYNTHESIS OF A HYDROCARBYLVINYLPHOSPHONIC ACID HYDROCARBYL ESTER

This is a continuation of application Ser. No. 08/386,392 filed Feb. 10, 1995, now abandoned.

BACKGROUND OF THE INVENTION

The known ester compounds of the type encompassed by the terminology used in the title, such as those of 1-phenylvinylphosphonic acid, are useful as intermediates for further chemical synthesis of, for example, plasticizers, flame retardants, and the like. Such compounds are also useful as comonomers, in minor amount, with a predominant amount of other vinylic monomers to impart flame retardancy and to alter the surface characteristics of the resulting polymer product. Various disclosures exist in regard to the process of formation of such compounds.

U.S. Pat. No. 2,365,466 to L. A. Hamilton describes their formation by reaction of an alcohol or phenol with a phosphonic acid dichloride.

British Patent No. 974,988 describes the formation of alpha, beta-unsaturated phosphonic acid esters, including certain 1-phenylvinyl phosphonic acid dialkyl ester compounds, by the reaction of an α-hydroxyphosphonic acid ester with thionyl chloride.

U.S. Abramov in Zh. Obshch. Khim, 22, pp. 709–712 (1952) discloses the reaction of aldehydes and ketones upon the salts of dialkyl phosphorous acids to form diesters of alpha hydroxyalkylphosphonic acids.

More recently, M. Yamashita et al. in Bull. Chem. Soc. Japan, 53, 1625–1628 (1980) described the Arbuzov reaction of trimethyl and triethyl phosphites with acyl chlorides to give 1-oxaalkylphosphonates which could be converted to vinylphosphonates by the Wittig reaction using methylenetriphenylphosphorane.

T. Hirao et al. in Bull. Chem. Soc. Japan, 55, 909–913 (1982) describe the palladium catalyzed reaction of aryl bromides with dialkyl phosphites in the presence of triethylamine to form dialkyl arylphosphonates and the similar treatment of vinyl bromides to give dialkyl vinylphosphonates.

SUMMARY OF THE INVENTION

In its broadest embodiment the present invention relates to the formation of hydrocarbylvinyl phosphonic acid hydrocarbyl esters which can be represented by the formula

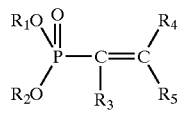

where any of $R_1$ through $R_5$ can independently be hydrogen, alkyl or aryl. Groups $R_1$ and $R_2$ can be joined together in a single cyclic structure bonded at each end thereof to the oxygens attached to the phosphorus atom (such as when neopentylene glycol is used as a reactant as described and claimed in U.S. Ser. No. 386,393, filed on even date herewith, and entitled "Neopentylene Phosphonate Compounds").

The present invention can be defined as a process for the synthesis of a hydrocarbylvinylphosphonic acid hydrocarbyl ester which comprises: (a) the base-catalyzed addition of a dihydrocarbyl phosphite to an aldehyde or ketone, such as acetophenone, to form a dihydrocarbyl 1-hydroxy hydrocarbylphosphonate compound, such as a dialkyl 1-hydroxy-1-phenylethyl-phosphonate; (b) the acid-catalyzed esterification, e.g., acetylation, of the compound from (a) with an acid anhydride, such as acetic anhydride, to form an esterified, e.g., acylated intermediate; and (c) the elimination of acid, e.g., by deacetylation, from the intermediate from (b) to form the desired hydrocarbylvinylphosphonic acid hydrocarbyl ester, such as a 1-phenylvinylphosphonic acid dialkyl ester.

Another embodiment of the present invention involves step (c) of the forgoing process in which carboxylic acid is removed from the intermediate to form the desired dialkyl ester product.

Still another embodiment of this invention is the base catalyzed reaction (a) in which an aldehyde or ketone and dihydrocarbyl phosphite are reacted using a nonnucleophilic strong organic base as catalyst.

DESCRIPTION OF PREFERRED EMBODIMENTS

The initial step in the process of the present invention comprises the reaction of a dialkyl phosphite of the formula

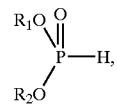

where $R_1$ and $R_2$ are each as defined above with both, preferably, being an unsubstituted or substituted alkyl group of no more than eight carbon atoms, e.g., most preferably from $C_1$ to $C_4$ alkyl, with an aldehyde or ketone of the formula

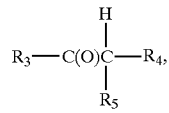

$R_3$, $R_4$, and $R_5$ being defined as set forth above, acetophenone being a preferred ketone, to form a dihydrocarbyl 1-hydroxy-hydrocarbylphosphonate of the formula

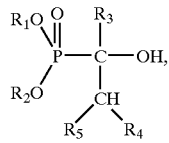

where each of the "R" groups depicted in the preceding formula is as defined before above. This step is practiced with base catalysis using, as a preferred class of catalyst, a nonnucleophilic strong organic base (such as one where the $pK_a$ of the conjugate acid is greater than about 10), such as 1,1,3,3-tetramethylguanidine. If desired, an alkali metal alkoxide catalyst (such as sodium ethoxide in ethanol solvent) in a suitable hydrocarbon solvent, such as hexane may also be used but it is less preferred. The reaction can be carried out at slightly below to slightly above ambient temperature (e.g., from 0° C. to 50° C.) with the desired product being recovered by recrystallization. The compound depicted above carries the following essential structure

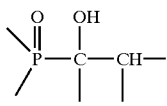

which allows for eventual elimination of the elements of water to form a phosphorus-substituted alkene.

The type of substituents on any of the "R" groups shown in the preceding formula can be selected from halo (such as chloro or bromo), if desired. The type of substituents that are contemplated for use on the phenyl group, if such is selected, for example as $R_3$, can be selected from halo (bromo or chloro), hydroxyl and alkyl.

The next step in the process of the invention involves the acid-catalyzed acetylation of the compound produced in the preceding step by its reaction with a suitable acid anhydride, such as acetic anhydride, to form an intermediate of the formula

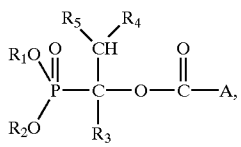

where the three "R" groups have the meanings given above, and A is derived from the acid anhydride used. In the case of acetic anhydride, A will be methyl. This reaction is preferably conducted at temperatures in the range of from about 10° C. to about 50° C., preferably using a strong acid (for example, one having a $pK_a$ of below about 1) as a catalyst. Such acid catalysts as a perhalic acid catalyst or a strong mineral acid, such as sulfuric acid can be used. The term "perhalic acid" is intended to encompass such acidic catalysts as perchloric acid and perbromic acid. Trifluoromethanesulfonic acid is another example of a catalyst that can be employed. Other acid catalysts which can be used include sulfonated macroreticular ion exchange resins (e.g., AMBERLYST 15, 35, or 36 brand resins), perfluorinated ion exchange powders (NAFION brand ion exchange materials), or acidic clays.

The intermediate from the previously described step, which, in a preferred embodiment, is a (1-dialkylphosphono-1-phenylalkyl carboxylate, for example, a (1-dialkylphosphono-1-phenylethyl acetate, is then converted to the desired 1-phenylvinylphosphonic acid dialkyl ester compound by deacetylation of the intermediate, preferably by heating at temperatures in the range of from about 50° C. to about 215° C. under reduced or atmospheric pressure (e.g., at about 50 to about 70 mm Hg pressure). The presence of a catalyst in the reaction medium will allow for the use of lower temperatures. Generally speaking, the use of higher temperatures within the above-described range will tend to give lower yields and poorer selectivities than the use of lower temperatures. At lower temperatures (e.g., at 50° C. to 125° C.), solid superacid catalysts (e.g., materials available under the trademarks AMBERLYST and NAFION) can be used to produce higher yields and higher selectivities of product than are achievable at the previously discussed higher reaction temperatures.

The following Examples further illustrate the present invention.

EXAMPLE 1

This Example illustrates the synthesis of diethyl 1-hydroxy-1-phenylethylphosphonate, a preferred compound which can be synthesized in the practice of the present invention.

Diethyl phosphite (167.2 gms, 1.21 moles), acetophenone (145.5 gms, 1.21 moles), and 80 cc of hexane were placed into a nitrogen-blanketed 500 cc reaction flask. The reaction mixture was then stirred, and 5.6 cc of saturated sodium ethoxide/2B ethanol catalyst was added in small aliquots over ninety minutes. The resulting exothermic reaction was controlled with an ice water bath. The temperature of the reaction mixture during the addition was kept at 16° to 18° C. After the addition of catalyst, the solution was allowed to crystallize with stirring for three and one-half hours. The crystals were then filtered, were washed with 150 cc of hexane, and were stripped at 25° C. and water aspirator pressure.

The yield of the first crystal crop, which was the substantially pure desired product, was 173.6 gms (54% of theory), M.P. 72°–72.5° C. The filtrate contained 61 mole % of the desired hydroxy adduct and 38% of unreacted diethyl phosphite, as analyzed by $^{31}P$ NMR spectroscopy.

EXAMPLE 2

This Example also illustrates the synthesis of diethyl 1-hydroxy-1-phenylethylphosphonate.

Diethyl phosphite (225.2 gms, 1.63 moles), acetophenone (195.9 gms, 1.63 moles), and 125 cc of hexane were placed in a similar set-up as described in Example 1. Addition of the sodium ethoxide catalyst was done stage-wise and crystals of the hydroxy adduct were collected as follows:

|  | Saturated Sodium Ethoxide (cc) | Crystal Yield (gms) |  |
| --- | --- | --- | --- |
| Stage 1 | 6.45 | 227.8 |  |
| Stage 2 | 1.1 | 81.3 |  |
| Stage 3 | 1.3 | 55.5 |  |
| Stage 4 | 0.66 | 17.0 |  |
| Total | 9.51 | 381.6 | (90.6% theory) |

EXAMPLE 3

This Example illustrates the acetylation and subsequent deacetylation of a hydroxy intermediate in the process of this invention.

A diethyl phosphite/acetophenone hydroxy adduct (10.0 gms, 0.0387 mole), which is also called "diethyl 1-hydroxy-1-phenylethylphosphonate" and whose method of preparation is given in Examples 1 and 2, and acetic anhydride (6.5 gms, 0.064 mole) were placed into a nitrogen-blanketed reaction flask. Then, 0.06 gm of 71.3% perchloric acid were added to the reaction mixture in two aliquots in about an hour. The reaction was then heated to 50° C. for eighty minutes, and the fully acetylated intermediate was placed under 70 mm of negative pressure and heated to 183° C. for two hours and fifteen minutes. Stripping of the resulting reaction mixture at 185°–187° C. continued for another six hours and fifteen minutes. The final reaction mixture contained 71 mole % (by $^{31}P$ NMR) of the desired diethyl 1-phenylvinylphosphonate (CAS Registry No. 25944-64-3).

EXAMPLE 4

This Example also illustrates the acetylation and subsequent deacetylation of a hydroxy intermediate in the process of this invention.

The hydroxy intermediate (10.0 gms, 0.0387 mole), which is also treated in Example 3 and whose method of preparation is given in Examples 1 and 2, and 10.0 gms (0.098 moles) of acetic anhydride, and 0.067 gm of concentrated sulfuric acid were added to the reaction apparatus described in previous Examples, and the resulting solution was stirred at room temperature for two hours and forty-five minutes. The reaction mixture was then placed under 70 mm of negative pressure and heated to 215° C. in one hour. Heating and stripping of the resulting reaction mixture at 215–217° C. continued for an additional three hours. The final crude reaction mixture contained 67.3 mole % (by $^{31}$P NMR) of the desired diethyl 1-phenylvinyl phosphonate.

EXAMPLE 5

Diethyl 1-hydroxy-1-phenylethylphosphonate (547.8 gms, 2.12 moles), whose preparation is described in Examples 1 and 2, and acetic anhydride (500 gms, 4.9 moles) were placed into a nitrogen-blanketed reaction flask. Then, 5.03 gms of 71% perchloric acid were added to the reactor in several aliquots in six hours and fifty-five minutes. The resulting mild exotherm was controlled with water cooling, and the temperature during addition was kept below 30° C. The reactor was then placed under 25–35 mm of pressure while the reactor temperature was slowly elevated to 190° C. (vapor temperature of 160° C.) over five hours. The deacetylated product (diethyl 1-phenylvinylphosphonate) was then removed by distillation at 185–195° C. (172–174° C. vapor temperature) at 25 to 1.0 mm Hg (a gradual decrease in pressure) over five additional hours. Six product fractions were collected with a total weight of 339.6 gms (96% purity of the diethyl ester by $^{31}$P NMR).

EXAMPLE 6

This Example illustrates another process for synthesis of the hydroxy intermediate described hereinbefore.

Diethyl phosphite (40.4 gms, 0.292 mole) and acetophenone (35.15 gms, 0.292 mole) were placed into a nitrogen-blanketed reaction flask. Then, 0.933 gm of 1,1,3,3-tetramethylguanidine catalyst was added in small aliquots over a period of six hours. The reaction was mildly exothermic to 26° C. The final sample, analyzed by $^{31}$P NMR, contained 84.1% diethyl-1-hydroxy-1-phenylethylphosphonate, the desired hydroxy intermediate, and 15.9% of the starting diethyl phosphite.

This hydroxy intermediate can be further treated in accordance with the procedure shown in Example 5.

EXAMPLES 7–8

These Examples illustrate additional synthesis procedures for the hydroxy intermediate described hereinbefore.

Diethyl phosphite (25.8 gms, 0.187 mole) and acetophenone (22.7 gms, 0.189 mole, 1 mole % excess) were placed in a nitrogen-blanketed dry reaction flask. The mixture was stirred and 0.42 gm (0.87% to combined weight of acetophenone and diethyl phosphite) of 1,1,3,3-tetramethylguanidine catalyst was added. The resulting mixture was heated slowly to 50° C. and held at that temperature for three hours. The reaction mixture was then allowed to cool to room temperature and about 25 gms of petroleum thinner (V.M. & P. brand naphtha) was added. The resulting composition was stirred at 25° C. for twenty-four hours with crystals forming spontaneously after about four and one-half hours. The crystals were filtered from the reaction mixture and were washed three times with small amounts of petroleum thinner. The washed crystals were then stripped of residual thinner at 25° C. and water aspirator pressure.

The following Table shows the % hydroxy intermediate as found by $^{31}$P NMR analysis for various samples taken from the reaction mixture for the above-described reading ("Run A") and for an analogous run ("B") where 1.7% catalyst was employed rather than 0.87%, at various times.

|              | Run No. |      |
| ------------ | ------- | ---- |
| Time (Hours) | A       | B    |
| 1.5          | —       | 60.4 |
| 3.0          | 58.7    | 59.8 |
| 6.5          | 72.3    | 80.0 |
| 9.0          | 81.2    | —    |
| 10           | —       | 93.5 |
| 24           | 97.2    | 98.7 |

The hydroxy intermediate can be further treated as shown in Example 5.

EXAMPLE 9

This Example illustrates an additional synthesis procedure for the previously described hydroxy intermediate.

Diethyl phosphite (40.4 gms, 0.292 mole) and acetophenone (35.15 gms, 0.292 mole) were placed into a nitrogen-blanketed reactor. Then, 0.93 gms of 1,1,3,3-tetramethylguanidine were added in small aliquots over a period of six hours. The reaction was mildly exothermic, and the temperature rose to 26° C. The reaction became unstirrable, and 35 gms of hexane were added, and the resulting slurry was then heated to 50° C. in fifteen minutes and was allowed to cool to room temperature. The yield of the hydroxy intermediate by $^{31}$P NMR was 97.9%.

EXAMPLE 10

This illustrates another procedure for synthesis of the hydroxy intermediate.

Diethyl phosphite (25.8 gms, 0.186 mole), acetophenone (22.7 gms, 0.188 mole), and VM&PNaphtha (24.0 gms) were placed into a nitrogen-blanketed flask. To the stirred reaction mixture was added 0.422 gms of 1,1,3,3-tetramethylguanidine in one aliquot. The reactor was then heated at 50° C. for three and one-half hours, then allowed to cool to 4° C. with stirring continued for total of twenty-seven hours. The $^{31}$P NMR results of the reaction slurry were as follows:

| Reaction time (hrs/min) | % (EtO)$_2$P(O)C(CH$_3$)(C$_6$H$_5$)OH | % (EtO)$_2$P(O)H |
| ----------------------- | -------------------------------------- | ---------------- |
| 3/00                    | 58.7                                   | 41.3             |
| 9/00                    | 81.2                                   | 18.8             |
| 24/00                   | 97.2                                   | 2.8              |

Filtration and washing of the white slurry with hexane afforded 40.9 gms (90.2% theory) of the hydroxy intermediate (100% purity by $^{31}$P NMR).

EXAMPLE 11

This Example illustrates acetylation/deacetylation of the hydroxy intermediate of Examples 9–10, for example.

Diethyl 1-hydroxy-1-phenylethylphosphonate (14.4 gms, 0.056 mole) and 63 gms of methylene chloride were placed into a 100 cc nitrogen-blanketed flask fitted with a magnetic stirrer, thermometer, and an additional funnel. The reactor was then cooled in an ice-water bath to 2° C., and 5.68 gms (0.056 mole) of concentrated sulfuric acid were added into the stirred reactor in small aliquots. Addition of sulfuric acid was completed in nine minutes, and temperature of the reactor rose to 5° C. Cooling of the reactor continued, and acetic anhydride (9.19 gms, 0.09 mole) was added within thirty-five minutes. The reaction flask was then heated at 50° C., and the composition of the mixture was analyzed by $^{31}P$ NMR with the following results observed:

| Reaction Time (hrs/min) | % Hydroxy Intermediate | % PVPA* Diethyl Ester | % PVPA Half Ester |
| --- | --- | --- | --- |
| 1/30 | 79.0 | 17.4 | — |
| 3/10 | 63.7 | 31.2 | — |
| 5/10 | 50.5 | 45.7 | 3.8 |
| 21/30 | 7.3 | 79.5 | 13.6 |

*PVPA is an abbreviation for 1-phenylvinylphosphonic acid.

EXAMPLE 12

This Example illustrates a preferred acetylation/deacetylation procedure for the hydroxy intermediate of Examples 9–10, for example.

Acetic anhydride (25 gms, 0.245 mole) and 1 hydroxy-1-phenylethylphosphonate (16.7 gms, 0.0647 mole) were placed into a nitrogen-filled reaction flask. The mixture was then stirred and cooled to 9° C. Then, 16.7 gms of AMBERLYST 15 strongly acidic ion-exchange resin, from Aldrich Chemicals, was added at once. The reaction was strongly exothermic and, even with ice-water cooling, the temperature rose to 45° C. The initial strong exotherm was over in seven minutes, and the mixture was heated at 75° C. as follows:

| Reaction Time (hrs/min) | % Acetylated Intermediate | % PVPA Diethyl Ester | % PVPA Half Ester | % PVPA |
| --- | --- | --- | --- | --- |
| 1/50 | 45.8 | 52.6 | 1.7 | — |
| 2/50 | 11.7 | 81.7 | 8.3 | 0.9 |
| 5/30 | 8.9 | 83.3 | 6.6 | 1.3 |
| 6/50 | 5.3 | 84.9 | 8.3 | 1.5 |
| * | 2.7 | 86.6 | 9.0 | 1.6 |

*These values indicate the composition of the reaction mixture after standing at 25° C. for an additional sixteen hours.

EXAMPLE 13

This Example constitutes a preferred embodiment for practice of the invention taken with Examples 12 and 14.

Acetic anhydride (250 gm, 2.45 moles) was placed into a one liter nitrogen-filled reaction flask. The liquid was then stirred, and AMERLYST 15 catalyst (83.5 gm) was added slowly. The temperature rose. When the temperature was below 30° C., 1-hydroxy-1-phenyl ethylphosphonate (167 gm, 0.65 mole) was added. the mixture was held at one and one half hours at room temperature and then the temperature was raised to 100° C. and held for the times given in the Table which follows:

| Reaction Time at 100° C. | % Acetylated Intermediate | % PVPA Diethyl Ester | % PVPA Half Ester | % PVPA |
| --- | --- | --- | --- | --- |
| 0 | 49.9 | 46.4 | 1.4 | 1.8 |
| 1 | 5.0 | 74.0 | 7.0 | 9.3 |
| 2 | 1.8 | 71.8 | 8.4 | 12.0 |

EXAMPLE 14

The same procedure used in Example 13 was employed except that in this Example only 42 gm of AMBERLYST brand catalyst was used. After adding the ingredients and holding the mixture for one and one half hours at room temperature, the temperature was raised to 125° C. The Table sets forth the results obtained:

| Reaction Time at 100° C. | % Acetylated Intermediate | % PVPA Diethyl Ester | % PVPA Half Ester | % PVPA |
| --- | --- | --- | --- | --- |
| 0 | 24.6 | 64.2 | 3.3 | 5.8 |
| 1 | 3.1 | 68.8 | 8.8 | 11.9 |
| 2 | 1.5 | 63.0 | 8.4 | 12.0 |

The foregoing Examples are presented for illustrative purposes only to exemplify certain embodiments of the present invention. The scope of protection sought is set forth in the claims which follow.

We claim:

1. A process for the synthesis of a hydrocarbylvinylphosphonic acid hydrocarbyl ester which comprises: (a) the base-catalyzed addition of a hydrocarbyl phosphite to an aldehyde or ketone to form a hydrocarbyl 1-hydroxy hydrocarbylphosphonate compound; (b) the acid-catalyzed esterification of the compound from (a) with an acid anhydride to form an esterified intermediate; and (c) catalyzed the removal of carboxylic acid from the intermediate from (b) to form the hydrocarbylvinylphosphonic acid hydrocarbyl ester.

2. A process for the synthesis of a 1-phenylvinylphosphonic acid dialkyl ester which comprises: (a) the base-catalyzed addition of a dialkyl phosphite to a methyl phenyl ketone to form a dialkyl 1-hydroxy-1-phenylalkylphosphonate compound; (b) the acid-catalyzed esterification of the compound from (a) with an acid anhydride to form an esterified intermediate; and (c) catalyzed the removal of carboxylic acid from the intermediate from (b) to form the 1-phenyl-vinylphosphonic acid dialkyl ester.

3. A process as claimed in claim 2 wherein the dialkyl phosphite contains no more than about eight carbon atoms in either of the alkyl groups therein.

4. A process as claimed in claim 2 wherein the dialkyl phosphite is diethyl phosphite.

5. A process as claimed in claim 2 wherein step (a) is base catalyzed using a nonnucleophilic strong organic base.

6. A process as claimed in claim 2 wherein step (b) is acid catalyzed using an acid catalyst having a $pK_a$ of below about 1.

7. A process as claimed in claim 2 wherein step (c) is performed at a temperature of from about 50° C. to about 215° C. in the presence of catalyst.

8. A process as claimed in claim 2 wherein the dialkyl phosphite contains no more than about eight carbon atoms in either of the alkyl groups therein, wherein step (a) is base catalyzed using an alkali metal alkylate and wherein step (b) is acid catalyzed using an acid catalyst having a $pK_a$ of below about 1.

9. A process as claimed in claim 8 wherein step (c) is performed at a temperature of from about 50° C. to about 215° C. in the presence of catalyst.

10. A process as claimed in claim 2 wherein the dialkyl phosphite is diethyl phosphite, the methyl phenyl ketone is acetophenone, and the acid anhydride is acetic anhydride.

11. A process as claimed in claim 10 wherein step (a) is base catalyzed using a nonnucleophilic strong organic base.

12. A process as claimed in claim 10 wherein step (b) is acid catalyzed using an acid catalyst having a $pK_a$ of below about 1.

13. A process as claimed in claim 10 wherein step (c) is performed at a temperature of from about 50° C. to about 215° C.

14. A process as claimed in claim 10 wherein step (a) is base catalyzed using an alkali metal alkylate and wherein step (b) is acid catalyzed using a perhalic acid catalyst.

15. A process as claimed in claim 14 wherein step (c) is performed at a temperature of from about 175° C. to about 215° C.

16. A process for the synthesis of a hydrocarbylvinylphosphonic acid hydrocarbyl ester which comprises the catalyzed removal of carboxylic acid from a 1-hydrocarbylphosphono-1-hydrocarbyl carboxylate to form the hydrocarbylvinylphosphonic acid hydrocarbyl ester.

17. A process for the synthesis of a 1-phenylvinylphosphonic acid dialkyl ester which comprises the catalyzed removal of carboxylic acid from a 1-dialkylphosphono-1-phenylalkyl carboxylate to form the 1-phenylvinylphosphonic acid dialkyl ester.

18. A process as claimed in claim 17 wherein the 1-dialkylphosphono-1-phenylalkyl carboxylate is a 1-acetoxy-1-phenylethenylphosphonic acid, diethyl ester.

19. A process as claimed in claim 17 wherein the removal of carboxylic acid is performed at a temperature of from about 50° C. to about 215° C. in the presence of catalyst.

20. A process for the synthesis of a 1-phenylvinylphosphonic acid dialkyl ester which comprises the base-catalyzed addition of a dialkyl phosphite to a phenyl ketone to form a dialkyl 1-hydroxy-1-phenylalkylphosphonate compound using a nonnucleophilic strong organic base as catalyst.

21. A process as claimed in claim 18 wherein the dialkyl phosphite contains no more than about eight carbon atoms in either of the alkyl groups therein.

22. A process as claimed in claim 20 wherein the dialkyl phosphite is diethyl phosphite.

23. A process as claimed in claim 20 wherein the dialkyl phosphite is diethyl phosphite and the ketone is acetophenone.

24. A process as claimed in claim 20 wherein the $pK_a$ of the conjugate acid of the catalyst is over about 10.

25. A process as claimed in claim 20 wherein the catalyst is 1,1,3,3-tetramethylguanidine.

* * * * *

UNITED STATES PATENT AND TRADEMARK OFFICE
CERTIFICATE OF CORRECTION

PATENT NO.    : 6,429,329 B1
DATED         : August 6, 2002
INVENTOR(S)   : Aaronson et al.

It is certified that error appears in the above-identified patent and that said Letters Patent is hereby corrected as shown below:

Column 8,
Lines 40 and 50-51, "catalyzed the" should read -- the catalyzed --

Signed and Sealed this

Third Day of December, 2002

JAMES E. ROGAN
*Director of the United States Patent and Trademark Office*